United States Patent [19]

Hull et al.

[11] Patent Number: 4,931,583
[45] Date of Patent: Jun. 5, 1990

[54] CITRATE ESTERS

[75] Inventors: Ezekiel H. Hull, Greensboro; Edward P. Frappier, Kernersville, both of N.C.

[73] Assignee: Morflex Chemical Compay, Inc., Greensboro, N.C.

[21] Appl. No.: 366,540

[22] Filed: Jun. 15, 1989

Related U.S. Application Data

[60] Continuation of Ser. No. 217,217, Jul. 11, 1988, Pat. No. 4,892,967, which is a division of Ser. No. 117,080, Nov. 4, 1987, Pat. No. 4,789,700, which is a continuation of Ser. No. 865,874, May 21, 1986, Pat. No. 4,711,922, which is a continuation of Ser. No. 735,149, May 17, 1985, abandoned, which is a continuation-in-part of Ser. No. 619,583, Jun. 11, 1984, abandoned.

[51] Int. Cl.$^5$ .......................................... C07C 69/704
[52] U.S. Cl. ................................. 560/180; 524/309; 524/310; 560/185; 560/204; 604/332
[58] Field of Search ........................................ 560/180

[56] References Cited

U.S. PATENT DOCUMENTS 3,056,818 10/1962 Werber ................................. 560/204
4,007,218 2/1977 Ghanayem et al. ................. 560/204

OTHER PUBLICATIONS

Chemical Abstracts, vol. 65, No. 5, 7374c, Aug. 1966.
Citrate Ester Development Products (Apr. 1982).
Citrate Ester Development Products (Oct. 1982)
Citrate Ester Development Products (Dec. 1983).

Primary Examiner—Werren B. Lone
Assistant Examiner—Vera C. Clarke

[57] ABSTRACT

Citrate esters are formed utilizing organic titanates as a catalyst allowing excess alcohol to be removed. Four citrate esters have been found which provide advantageous plasticizing properties to PVC compositions which include superior toxicity test results and superior soapy water extraction test results. The four citrate esters are: acetyltri-n-hexyl citrate, n-butyryltri-n-hexyl citrate, acetyltri-n-(hexyl/octyl/decyl) citrate, and acetyltri-n-(octyl/decyl) citrate. Articles formed from the PVC plasticized mixtures are extremely useful in the medical or health care field as they demonstrate a low order of toxicity.

15 Claims, 1 Drawing Sheet

CITRATE ESTERS

This is a continuation of application Ser. No. 07/217,217 filed 11 July 1988 now U.S. Pat. No. 4,892,967 which was a divisional application of Ser. No. 07/117,080 filed 04 November 1987 now U.S. Pat. No. 4,789,700 which was a continuation of Ser. No. 06/865,874 filed 21 May 1986, now U.S. Pat. No. 4,711,922 which was a continuation of pending patent application Ser. No. 06/735,149 filed 17 May 1985, now abandoned which was a continuation-in-part of application Ser. No. 06/619,583 filed 11 June 1984, also now abandoned.

BACKGROUND OF THE INVENTION

1. Field of the Invention

Citrate esters are useful as plasticizers for polyvinyl chloride (PVC) resins as certain of these esters provide a low order of toxicity when compared to phthalate esters which have been conventionally used. Other advantages have been noted using certain citrate esters as plasticizers in PVC compositions and articles, including improved resistance to soapy water extraction and low temperature and transport properties.

The preparation of the citrate esters has been found to be significantly enhanced by the utilization of certain organic titanate catalysts which allow the excess alcohol to be removed after the esterification step.

2. Description of the Prior Art and Objectives of the Invention

Citrate esters commercially produced using citric acid have long been available and have been used as plasticizers for PVC resins. However, the performance of articles produced from the PVC resin compositions whether utilizing citrate esters known to date or conventional phthalate plasticizers have had many inherent disadvantages. For example, medical-grade PVC compositions are used to form blood bags, tubing and a variety of health-related articles and in recent years toxicity has been a major concern for manufacturers of such articles. Recent reports have identified di-2-ethylhexyl phthalate (DEHP) or (DOP) and di-2-ethyl-hexyl adipate (DEHA) as hepatocarcinogens in rodents. While certain of the phthalates have excellent plasticizing qualities, their suspected carcinogenic nature renders them doubtful candidates for future medical-grade uses. As an alternative, known citric acid esters such as acetyltri-n-butyl and tri-n-butyl citrate were tried as PVC plasticizers in medical-grade applications but it was deterimined that these compounds were not entirely satisfactory due to their high soapy water extraction percentages and would therefore not be useful in many medical area applications. Also, it has been found that new production techniques had to be devised for the newer citric acid esters which were determined to have suitable toxicity and physical characteristics when used as PVC plasticizers.

It is therefore an objective of the present invention to provide PVC plasticizers which provide superior toxicity test results in biological studies.

It is also an objective of the present invention to provide plasticizers for PVC compositions which can be processed without difficulty using conventional extrusion, calendering, or plastisol techniques.

It is yet another objective of the present invention to provide new citric acid esters namely: acetyltri-n-hexyl citrate, n-butyryltri-n-hexyl citrate, acetyltri-n-(hexyl/octyl/decyl) citrate, and acetyltri-n-(octyl/decyl) citrate which can be used as plasticizers having desirable physical characteristics when imparted into PVC compositions.

It is still another objective of the present invention to provide PVC compositions and formed articles therefrom having superior results in toxicology studies concerning dermal toxicity, oral toxicity and genetic assays.

It is also an objective of the present invention to provide a new process for the low temperature manufacture of the four new citric acid esters utilizing organic titanates to provide economical and efficient production methods.

Others objectives and advantages of the present invention will be demonstrated to those skilled in the art as set forth in detail below.

SUMMARY OF THE INVENTION

Citrate esters of the formula:

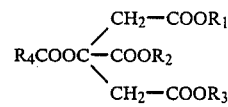

where $R_1$, $R_2$, and $R_3 = CH_3$ to $C_{18}H_{37}$, $R_4 = CH_3$ to $C_7H_{15}$, and more specifically acetyltri-n-hexyl citrate, n-butyryltri-n-hexyl citrate, acetyltri-n-(hexyl/octyl/decyl) citrate, and acetyltri-n-(octyl/decyl) citrate are produced utilizing an organic titanate catalyst and such esters have been found useful as medical-grade plasticizers in PVC compositions. The plasticizers have a low order of toxicity and inpart to PVC the proper balance of physical properties needed in health care and medical-grade uses. The production steps for the citric acid esters include low temperature esterification at 140° C. or below, removal of any excess alcohol and thereafter, alkoxylation. Conventional neutralization and finishing steps are then carried out. The alkoxylation step is carried out at a temperature less than approximately 110° C.

A PVC resin can be combined with one of the above-mentioned citric acid esters, along with suitable stabilizers and lubricants, to form a plasticized PVC which can be extruded, calendered or otherwise processed into suitable articles of manufacture including blood bags, tubing and other products. Articles so made have a low order of toxicity and provide superior extraction properties, particularly in soapy water extraction tests. The soapy water extraction test is a standard test, the results of which closely resemble the results obtained with body fluids such as human blood.

DESCRIPTION OF THE PREFERRED EMBODIMENTS

Figure 1:
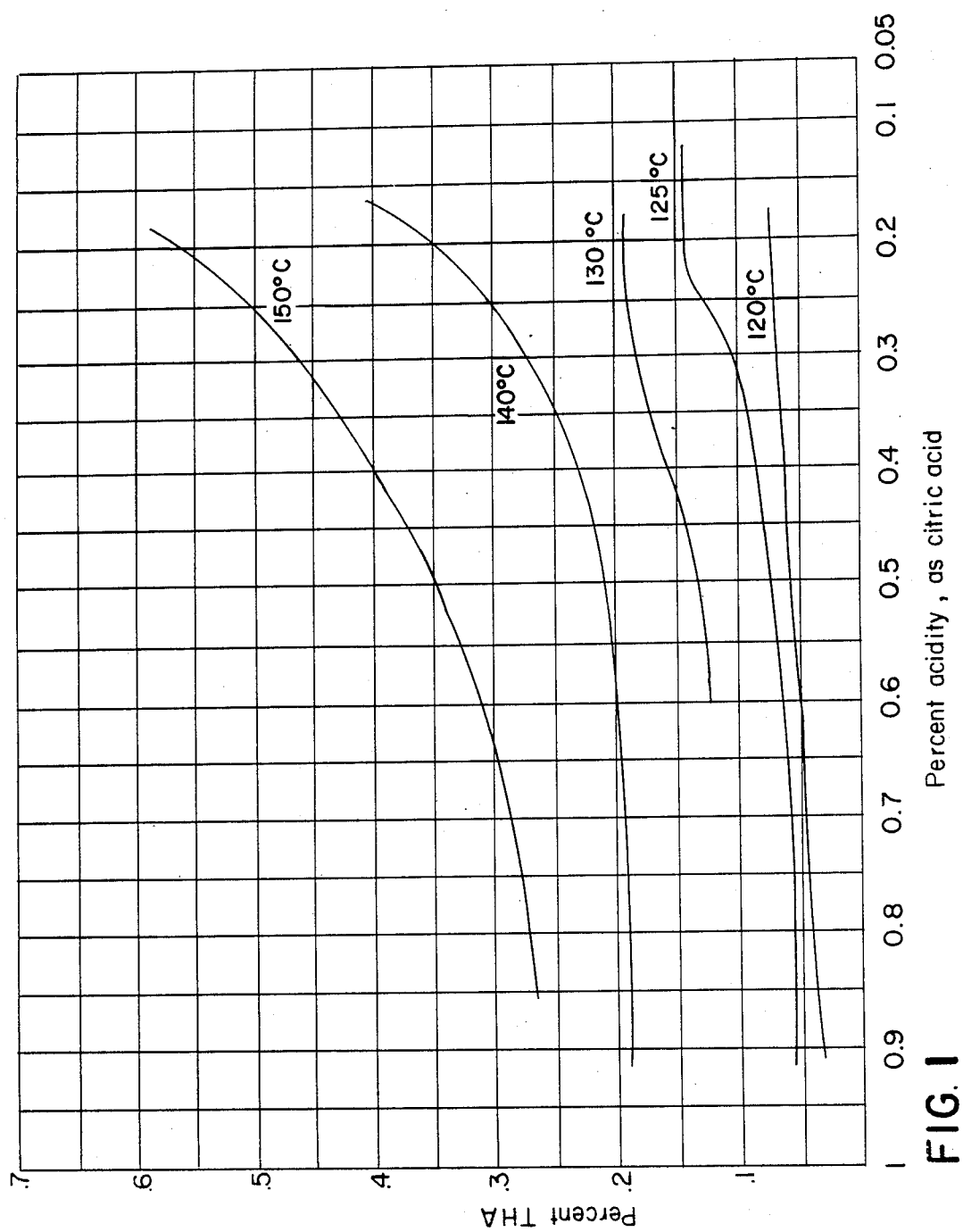
FIG. 1 illustrates a graph showing the percent THA versus percent acidity, as citric acid, of the reaction of n-hexyl alcohol and citric acid at various temperatures.

The four preferred forms of the citrate esters are as follows:

1. acetyltri-n-hexyl citrate:

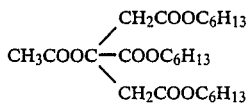

2. n-butyryltri-n-hexyl citrate:

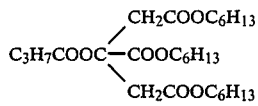

3. acetyltri-n-(hexyl/octyl/decyl) citrate:

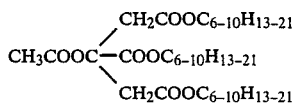

4. acetyltri-n-(octyl/decyl) citrate:

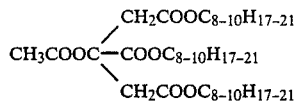

The preferred method of manufacture of the above-identified citrate esters comprises low temperature esterification below 150° C. and preferably at a temperature range of from 125° C. to 130° C. of the proper alcohol (such as n-hexyl alcohol for acetyltri-n-hexyl citrate) with citric acid in the presence of the organic titanate, tetra-n-butyl titanate, removal of any excess n-hexyl alcohol, and then alkoxylation of the esters produced with an acid anhydride. At esterification temperatures above 150° C. citrates undergo rapid degradation resulting in numerous products of decomposition. At temperatures somewhat below 150° C. the major decomposition product is an aconitate ester. The alkoxylation takes place at a temperature of below approximately 110° C. Tetra-n-butyl titanate is preferred since the ester interchange which takes place between the titanate alkyl groups and citrate alkyl groups does not result in the introduction of alkyl groups not normally present in the citrate esters.

The preferred PVC composition comprises blending and milling a medium molecular weight PVC resin with one of the above citrate esters on a two to one ratio, resin to plasticizer, along with stabilizers, lubricants and extenders as required. Articles manufactured from the preferred PVC compositions include blood bags, tubing and other articles for the medical and health care fields.

DETAILED DESCRIPTION OF THE INVENTION

Certain citrate esters, namely acetyltri-n-hexyl citrate, n-butyryltri-n-hexyl citrate, acetyltri-n-(hexyl/octyl/decyl) citrate and acetyltri-n-(octyl/decyl) citrate have been found to be particularly useful in medical applications when compounded with PVC resins through conventional plastisol, calendering or extrusion techniques. Such plasticized PVC exhibits good clarity, good low temperature properties, low volatility and low extractability into various media. Also, a low order of acute toxicity has been shown and complete compatibility with medium molecular weight PVC resins make the four named esters unique and valuable. Studies have shown that the four citrate esters are not toxic substances, primary skin irritants or ocular irritants to unrinsed eyes and oral administration has produced no signs of systemic toxicity and has shown no mortality in fasted mice or rats. Genetic toxicology assays for detecting mutagenic activity at the gene or chromosomal level have shown that these esters do not induce gene mutation in either microbial cells or in mammalian cells in vitro or chromosomal mutation in vivo or in vitro. Studies have also shown that under in vivo conditions, these citrate esters hydrolyze rapidly and completely in concentrations at expected realistic levels of human exposure.

Preparation of the citrate esters are as follows:

EXAMPLE 1

Preparation of acetyltri-n-hexyl citrate 330 lbs. of n-hexyl alcohol, 180 lbs. of citric acid and 1.54 lbs. of tetra-n-butyl titanate and 15 gallons of heptane are charged to a vessel equipped with agitator, thermometer, vapor column, condenser and a decanter set to allow removal of water formed during the reaction while refluxing heptane. The esterification is effected at 140° C. to maintain the aconitate (THA) level below 0.5% for general production. As shown in FIG. 1 the aconitate level can be kept well below the 0.2% range by longer reaction times at lower temperatures with the optimum time, and aconitate levels reached by temperatures of from approximately 125° C. to 130° C. As shown, at a temperature of approximately 130° C. a unique result is achieved in that the aconitate formation levels out to provide a citrate ester having excellent purity. During esterification water is periodically removed from the decanter in order to maintain proper temperature and reaction rates. The esterification is continued until the esterification mixture tests 0.5% maximum acidity calculated as citric acid although lower temperature esterification and acidity percentage may be used for higher purity products as mentioned above. Next, the vessel is cooled to 120° C. and any water is removed from the separator and any heptane therein is also removed for future use. The reflux line of the vessel is closed and pressure on the system is reduced slowly. The kettle is heated to 130°-140° C. and steam is introduced to help remove any residual alcohol. This vacuum steam stripping is continued until alcohol cannot be detected by conventional laboratory tests. When no more alcohol can be found, the steam is discontinued and the temperature is reduced to 100° C. and the vacuum is broken with nitrogen gas.

Next, 0.4 lb. concentrated sulfuric acid ($H_2SO_4$) is charged into the vessel after which it is sealed and approximately 107 lbs. of acetic anhydride (in a determined molar amount) are added at a slow rate so that the temperature does not exceed 110° C. When all the anhydride has been added, agitation of the mix continues for approximately one hour until the acetylation reaction has been completed.

Next, a full vacuum is put on the system and enough heat is added for distillation to proceed at a suitable rate. This step continues until acetic acid is shown to be 5% or less by conventional lab tests whereupon the mixture is cooled to 75° C. for neutralization.

The remaining steps of neutralization, bleaching, washing, etc. are carried out as in conventional esterification processes.

EXAMPLE 2

Preparation of n-butyryltri-n-hexyl citrate

The vessel used in example 1 is again charged with 330 lbs. of n-hexyl alcohol, 180 lbs. of citric acid and 1.54 lbs. of tetra-n-butyl titanate. Esterification is carried out as in example 1 as is the heptane-alcohol strip. Butyrylization is thereafter done with the addition of 0.4 lbs. of concentrated sulfuric acid and 166 lbs. of n-butyryic anhydride as shown above in the acetylation process. The butyric acid may be removed as shown above or by neutralization.

Examples 1 and 2 produce esters with the following characteristics:

| | ANALYTICAL DATA | |
|---|---|---|
| Property | Acetyltri-n-hexyl Citrate | n-Butyryltri-n-hexyl Citrate |
| Purity wt % | 99 | 99 |
| Color APHA | 50 max. | 50 max. |
| Neut. No. mg KOH/g | 0.2 max. | 0.2 max. |
| Moisture K.F. | 0.25 max. | 0.25 max. |
| S. G. @ 25/25° C. | 1.0045–1.0055 | 0.991–0.995 |
| R. I. @ 25/25° C. | 1.445–1.447 | 1.444–1.448 |
| Viscosity @ 25° C. cps | 25–35 | 25–35 |
| Odor @ 25° C. | Little or none | Little or none |
| Heat Stability (2 Hrs. @ 150° C.) | | |
| Color APHA | 50–60 | 50–60 |
| Neut. No. mg KOH/g | 0.2 max. | 0.2 max. |
| Odor @ 25° C. | Mild | Mild |

It has been determined that a citrate ester yield can be achieved of 99+% purity with a minimum of aconitate formation and unacetylated esters by lowering the esterification temperatures to 130° C. or below with a preferable temperature range of 125° C. to 130° C. Table A and FIG. 1 demonstrate the percentage of tri-n-hexyl aconitate (THA) formed during the production of acetyltri-n-hexyl citrate whereby the reaction is terminated at approximately 2% acidity, as citric acid. As shown in Table A and FIG. 1 below, the aconitate levels range from approximately 0.14 to 0.19 with a reaction time of from 25 to 19 hours at temperatures of from 125° C. to 130° C. It has been determined that by lowering the temperature from 140° C. to 130° C. an additional reaction time of only 90 minutes is required with the aconitate level dropping from 0.35 to 0.19%, a decrease of approximately 45%. As shown, the aconitate level can be tremendously decreased by lowering the temperature approximately 10 degrees from 140° C. to 130° C. without substantially increasing the reaction time based on 0.2% acidity (citric acid) as the reaction completion indicator. As shown in FIG. 1 a stabilization of the aconitate formation occurs during esterification at a critical temperature of approximately 130° C. providing a technique for the manufacture of high purity esters having low aconitate levels. Lower aconitate percentages and other impurities provide the high quality plasticizer needed for medical-grade products.

TABLE A

Reaction Time and Aconitate Formation Rates at Various Temperatures

| Esterification Temperature (°C.) | Reaction Time (Hrs.) | Final THA Content (%) | % Acidity As Citric Acid |
|---|---|---|---|
| 120 | 24¼ | 0.07 | 0.17 |
| 125 | 25 | 0.14 | 0.17 |
| 130 | 19 | 0.19 | 0.17 |
| 140 | 17½ | 0.41 | 0.16 |
| 150 | 13 | 0.59 | 0.19 |

It is believed that acids such as citric acid with low pk values exhibit a synergistic effect with titanate catalysts at low temperature in the 150° C. or lower range. Phthalic acid which has a high pk value will not undergo esterification with the titanate catalysts at these low temperatures.

Also, other organic titanate catalysts can be used to produce the four (4) esters of this invention such as tetrakis-2-ethylhexyl titanate although superior results have been demonstrated using tetra-n-butyl titanate.

| PREPARATION AND TESTING OF PVC COMPOSITIONS | |
|---|---|
| FORMULATION | PARTS BY WEIGHT |
| Resin (Medium Molecular Weight PVC) | 100 |
| Plasticizer | 50 |
| Stabilizer (Calcium/Zinc) | 2.5 |
| Lubricant (stearic acid) | 0.25 |

The above formulation was blended and milled for 5–10 minutes at 325° to 340° F. The milled stock was pressed (3 min. at 340°–360° F. and 32,000 psi) to 40- and 70-mil sheets, and aged for 48 hours at room temperature for evaluation. All tests were made with samples cut from 70-mil pressed stock except for extraction tests which were obtained on 40-mil samples. The performance data was obtained by accepted ASTM methods with modifications as detailed below in Table B.

| | |
|---|---|
| Tensile Strength Ultimate Elongation Modulus (100% elongation) (ASTM D638) | Determined with Instron TT, 1100 series (2 in./min.) using a dumbbell-shape specimen. Test carried out at 70° ± 5° F. |
| Hardness (ASTM D676) | Determined with Shore Durometer A (10 sec.) at 75° ± 5° F. |
| Torsional Flex (T$_4$ and T$_f$) (ASTM D1043) | Determined with Torsion Flex Tester of Clash and Berg design. T$_4$ is the temperature at which the Modulus of Rigidity is 10,000 psi; T$_f$ is the temperature at which the Modulus of Rigidity is 100,000 psi. |
| Brittle Point (ASTM D746) | Determined by impact method using Scott Tester, Model E. |
| Volatile Loss (A/C) (ASTM D1203) | Determined on specimens 2 inches in diameter heated in activated carbon at 70° C. for 24 hours. Results are expressed as percent of plasticizer lost. |
| Water extraction (Tap) Soapy Water Extraction (1% Ivory Flakes) Oil Extraction (ASTM NO. 3) | Determined on specimens 2 inches in diameter suspended in appropriate liquid at 60° C. for 24 hours. Results are expressed as percent of plasticizer lost. |
| Migration Loss (silica) | Determined on specimens 2 inches in diameter heated in silica (100 mesh), at 70° C. for 24 hours. Results are expressed as percent of plasticizer lost. |
| Volatile Loss (air) | Determined by Oven Method (24 hr. at 100° C.) on specimens 2 inches in diameter. Results are expressed as percent of plasticizer lost. |

TABLE B

| (PLASTICIZER PERFORMANCE DATA) | | | | | | | |
|---|---|---|---|---|---|---|---|
| PLASTICIZER | DEHP | DEHA | #1 | #2 | #3 | #4 | #5 |
| HARDNESS, Durometer A, 10 Sec. | 79 | 78 | 78 | 81 | 81 | 87 | 87 |
| TENSILE, psi | 2748 | 1797 | 2862 | 2978 | 2924 | 2743 | 2789 |
| ULTIMATE ELONGATION, % | 395 | 414 | 400 | 390 | 427 | 364 | 374 |
| 100% MODULUS, psi | 1368 | 1092 | 1348 | 1574 | 1362 | 1656 | 1704 |
| $T_4$ (10,000 psi), °C. | −8.4 | −30.8 | −7.6 | −9.1 | −11.9 | −6.9 | −4.0 |
| $T_f$ (100,000 psi), °C. | −38.8 | −66.5 | −35.6 | −41.6 | −48.7 | −53.1 | −59.7 |
| BRITTLE POINT, °C. | −24.5 | −56.5 | −18.5 | −26.0 | −33.5 | −36.8 | −37.8 |
| VOLATILE LOSS, (air), % | 4.8 | 7.1 | 12.1 | 2.6 | 1.7 | .3 | .1 |
| VOLATILE LOSS, (A/C), % | 3.4 | 7.6 | 7.0 | 1.7 | 1.4 | 2.8 | 4.5 |
| WATER EXTRACTION, % | .7 | 1.5 | 1.2 | 1.9 | 1.7 | 1.5 | 3.3 |
| SOAPY WATER EXTRACTION, % | 2.7 | 11.0 | 9.5 | 5.4 | 2.2 | 3.4 | 2.4 |
| OIL EXTRACTION, % | 11.4 | 34.7 | 10.9 | 13.8 | 15.7 | 15.2 | 19.3 |
| SILICA GEL MIGRATION, % | 12.2 | 23.0 | 17.0 | 4.4 | 3.6 | 4.8 | 7.4 |

1 - acetyltri-n-butyl citrate
2 - acetyltri-n-hexyl citrate
3 - n-butyryltri-n-hexyl citrate
4 - acetyltri-n-(hexyl/octyl/decyl) citrate
5 - acetyltri-n-(octyl/decyl) citrate The plasticizer performance data in Table C demonstrates the results of tests with citric esters/epoxidized soybean oil (ESO) blends. ESO is commonly used in conjunction with DEHP at levels in the range of 1-5% based on DEHP as an aid in stabilization. The ratio of 2.5/97.5 ESO/citrate was used as a base point in the studies. Test results on this combination are shown in column 1. A significant improvement in properties, particularly soapy water extraction is noted.

TABLE C

| (PLASTICIZER PERFORMANCE DATA) | | | | | |
|---|---|---|---|---|---|
| PLASTICIZER PERCENTAGES: | 2.5 ESO 97.5 #2 | 20 ESO 80 #2 | 0 ESO 60 #2 | 40 ESO 60 #3 | 40 ESO 60 #5 |
| HARDNESS, Durometer A, 10 Sec. | 81 | 80 | 80 | 81 | 85 |
| TENSILE, psi | 2907 | 3010 | 3079 | 3165 | 3097 |
| ULTIMATE ELONGATION, % | 422 | 424 | 420 | 428 | 395 |
| 100% MODULUS, psi | 1415 | 1429 | 1491 | 1514 | 1779 |
| $T_4$ (10,000 psi), °C. | −9.5 | −7.8 | −7.7 | −8.2 | −5.4 |
| $T_4$ (100,000 psi), °C. | −41.8 | −41.3 | −39.3 | −41.8 | −50.3 |
| BRITTLE POINT, °C. | −26.5 | −25.5 | −20.5 | −24.5 | −26.5 |
| VOLATILE LOSS, (Air), % | 2.4 | 2.1 | 1.5 | .8 | .5 |
| VOLATILE LOSS, (A/C), % | 1.3 | 1.6 | 1.4 | .9 | 1.1 |
| WATER EXTRACTION, % | 1.3 | .9 | .6 | .8 | 1.0 |
| SOAPY WATER EXTRACTION, % | 2.9 | 2.9 | 6.4 | 4.8 | 3.8 |
| OIL EXTRACTION, % | 13.0 | 11.6 | 10.1 | 10.0 | 12.9 |
| SILICA GEL MIGRATION, % | 5.7 | 5.3 | 4.7 | 4.0 | 2.5 |

ESO - Ester/epoxidized Soybean Oil
2 - acetyltri-n-hexyl citrate
3 - n-butyryltri-n-hexyl citrate
5 - acetyltri-n-(octyl/decyl) citrate Since ESO is less expensive than citrates, a reduction in plasticizer cost results if ESO can be substituted for part of the citrates. Results of tests with higher ESO/citrate ratios as shown in columns 2-5 of Table C and a significant improvement in properties up to and perhaps beyond the ratio of 20/80 ESO/citrate ratio as shown.

Various other PVC compositions can be formulated and the examples and illustrations shown herein are for illustrative purposes and are not intended to limit the scope of the invention.

We claim:

1. A citrate ester of the formula:

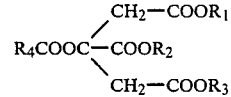

where $R_1$, $R_2$, and $R_3 = CH_3$ to $C_{18}H_{37}$, $R_4 = CH_3$ to $C_7H_{15}$, wherein said ester has heat stability characteristics, after heating at 150° C. for two hours, of a color not greater than 50-60 APHA and a mild odor at 25° C.

2. The ester of claim 1 wherein said ester is selected from the group consisting of acetyltri-n-butyl citrate, acetyltri-n-hexyl citrate, n-butyryltri-n-hexyl citrate, acetyltri-n-(hexyl/octyl/decyl) citrate, and acetyltri-n-(octyl/decyl) citrate.

3. The ester of claim 1 wherein said ester is acetyltri-n-butyl citrate.

4. The ester of claim 1 wherein said ester is acetyltri-n-hexyl citrate.

5. The ester of claim 1 wherein said ester is n-butyryltri-n-hexyl citrate.

6. The ester of claim 1 wherein said ester is acetyltri-n-(hexyl/octyl/decyl) citrate.

7. The ester of claim 1 wherein said ester is acetyltri-n-(octyl/decyl) citrate.

8. A citrate ester of the formula:

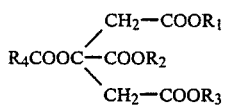

where $R_1$, $R_2$, and $R_3 = CH_3$ to $C_{18}H_{37}$, $R_4 = CH_3$ to $C_7H_{15}$, said ester having an aconitate level of less than 0.20% when the esterification mixture from which said citrate is produced tests about 0.6% maximum acidity calculated as citric acid, said citrate having heat stability characteristics, after heating at 150° C. for two hours, of a color not greater than 50–60 APHA and a mild odor at 25° C.

9. The citrate ester of claim 8 selected from the group consisting of acetyltri-n-butyl citrate, acetyltri-n-hexyl citrate, n-butyryltri-n-hexyl citrate, acetyltri-n-(hexyl/octyl/decyl) citrate, and acetyltri-n-(octyl/decyl) citrate.

10. The citrate ester of claim 8 consisting of acetyltri-n-butyl citrate.

11. The citrate ester of claim 8 consisting of acetyltri-n-hexyl citrate.

12. The citrate ester of claim 8 consisting of n-butyryltri-n-hexyl citrate.

13. The citrate ester of claim 8 consisting of acetyltri-n-(hexyl/octyl/decyl) citrate.

14. The citrate ester of claim 8 consisting of acetyltri-n-(octyl/decyl) citrate.

15. A citrate ester of the formula:

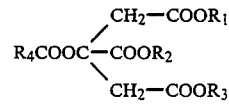

where $R_1$, $R_2$, and $R_3 = CH_3$ to $C_{18}H_{37}$, $R_4 = CH_3$ to $C_7H_{15}$, wherein said ester has a heat stability characteristic, after heating at 150° C. for two hours, of a mild odor at 25° C.

* * * * *